United States Patent [19]

Ronning et al.

[11] Patent Number: 4,765,982

[45] Date of Patent: Aug. 23, 1988

[54] INSECT CONTROL DEVICE

[75] Inventors: Patricia M. Ronning, St. Paul; Gregg A. Vandesteeg, Roseville, both of Minn.

[73] Assignee: Minnesota Mining and Manufacturing Company, St. Paul, Minn.

[21] Appl. No.: 71,629

[22] Filed: Jul. 9, 1987

Related U.S. Application Data

[62] Division of Ser. No. 373,533, Apr. 30, 1982, Pat. No. 4,683,132.

[51] Int. Cl.$^4$ ............................................. A01N 25/34
[52] U.S. Cl. ................................... 424/403; 424/402; 424/405; 424/407; 424/408; 514/781
[58] Field of Search ................ 424/403, 405, 407, 408

[56] References Cited

U.S. PATENT DOCUMENTS 3,719,751  3/1973  Rauscher et al. ................... 424/403
4,436,719  3/1984  Lindaberry ......................... 424/407

Primary Examiner—Sam Rosen
Attorney, Agent, or Firm—Donald M. Sell; James V. Lilly

[57] ABSTRACT

Compositions, devices, and methods are disclosed for controlling insect activity wherein an insect control agent is self-adhered to a rough-surfaced fiber. Preferably the fiber is a graft polymer of cellulose and an ethylenically unsaturated material copolymerizable with cellulose. The invention provides extended control of insect activity.

1 Claim, No Drawings

INSECT CONTROL DEVICE

This is a division of application Ser. No. 373,533 filed Apr. 30, 1982, now U.S. Pat. No. 4,683,132.

TECHNICAL FIELD

This invention relates to the control of insect activity. More particularly it relates to compositions, devices, and methods for extended control of insect activity wherein rough-surfaced fibers having a sustained release insect control agent self-adhered thereto are employed. The devices of the invention may be provided in the form of webs, sheets, mats, fabrics, and the like, which may be either woven or non-woven.

As used throughout this application, the following terms have the following meanings:

"Insect" means crawling and/or flying pests such as wasps, hornets, ants (including fire ants), spiders (particularly web-making spiders), house flies, mosquitoes, cockroaches, and the like.

"Control" means either the killing or repelling of such insects.

BACKGROUND ART

Insect control has been a desired goal of mankind throughout history. Early attempts at control involved placing sticky substances at locations where insects would be required to pass. Such attempts are believed to have lead to the development of the product which came to be known as "fly paper" which is merely a strip of material covered with a sticky substance. Such a product is described in U.S. Pat. No. 813,116 issued in 1906 to Julius H. Bien.

Another method of controlling insects involved catching them in traps which may include an attractant and a tacky substance. Such traps have become more and more sophisticated and complex. For example, see U.S. Pat. No. 3,755,958.

A common present-day means for controlling insects involves application of insect control agents either by vaporization or by application to a suitable carrier strip or device. Vaporization may be accomplished by the use of conventional aerosol dispensers or by means of plastic strips which exude vapors of the insect control agent. Vaporization by the former technique has its disadvantages in that there is very little control over the dispersal of the control agent so that it may spread into areas where it is not wanted. Additionally, this technique does not provide for sustained insect control. Vaporization by the latter technique has its disadvantages in that the insect control agent either does not firmly adhere to the plastic strips or the plastic strips are not resistant to environmental degradation. In the former situation the agent may be readily dislodged from the substrate by environmental causes such as wind or rain. In the latter situation the substrates have short useful lives. In both situations the resulting devices do not provide sustained release of the insect control agent under outside environmental conditions.

Various techniques have been suggested for providing sustained release of insect control agents. For example, U.S. Pat. No. 4,056,610 discloses a microcapsule insecticide composition in which a pyrethroid permeates a porous shell wall and maintains an insecticidally effective level of the pyrethroid upon the outer surface of the shell wall for an extended period of time. Control is achieved by killing insects which contact the pyrethroid released through the capsule wall. For this purpose, the capsules are spread about in various ways with the purpose of contacting insects. Although this patent mentions incorporating microcapsules in sheet materials such as tapes, the present invention provides an improvement thereover.

U.S. Pat. No. 4,103,450 discloses the use of insecticide materials on the surface of a low density web of synthetic fibers. These devices are installed so that they will create a lethal zone for the insect to pass through and be exposed to the insecticide. These devices are useful for certain purposes but they suffer from the disadvantage that they do not stand up well to the rigors of outside environmental conditions.

DISCLOSURE OF THE INVENTION

In accordance with the present invention there are provided compositions, devices, and methods for providing extended control of insect activity wherein rough-surfaced fibers are employed which have a sustained release insect control agent self-adhered thereto. The compositions and devices of the invention are preferably resistant to weathering and deterioration. Additionally, they provide long lasting insect control and, preferably, demonstrate broad spectrum activity. Furthermore, the compositions, devices, and methods of the invention also encourage insects to abandon already established nests, hives, combs and the like.

The compositions and devices of the invention include either single fibers or groups of fibers. Generally groups of fibers are used for insect control. They may be provided from a solution, suspension, or aerosol. Alternatively, they may be provided directly as a solid or as a preformed woven or non-woven group of fibers.

The compositions and devices of the invention control insect activity by providing an effective level of the control agent in the area where control is desired for an extended period of time.

DETAILED DESCRIPTION

The fibers useful in the present invention are rough-surfaced fibers. Thus, they exhibit an uneven or contorted surface as opposed to the even or smooth surface exhibited by synthetic fibers such as polyethylene, polyvinyl alcohol, and polyester. Preferably the fibers are formed from either synthetically prepared or naturally occurring cellulosic fiber-forming materials. Such fibers are oleophilic.

Blends of rough-surfaced and smooth-surfaced synthetic fiber-forming materials may also be used in the present invention. Examples of useful smooth-surfaced synthetic fiber-forming materials include polymeric materials such as polyethylene, polyvinyl alcohol, polyester, nylon, polyvinylfluoride, polyacrylate, and the like.

While both cellulosic rough-surfaced fiber-forming materials and blends thereof with smooth-surfaced synthetic-fiber forming materials are useful, they exhibit limited strength and are susceptible to attack by microbes such as bacteria, fungi, and molds. Additionally, certain of such materials do not exhibit good resistance to environmental conditions such as wind and water.

A class of fiber-forming materials has been found which is particularly resistant to degradation. This class of materials comprises graft polymers of cellulose and ethylenically unsaturated materials copolymerizable therewith. The graft polymers have a combination of desirable properties for use in the present invention.

Moreover, the graft polymers may be blended with other fibers such as non-grafted cellulosic fibers. The graft polymers most preferably comprise copolymers of essentially fully bleached cellulose and one or more ethylenically unsaturated monomers.

Ethylenically unsaturated materials which may be grafted to cellulose include, for example, acrylates such as methyl acrylate, ethyl acrylate, butyl acrylate, n-butyl acrylate, acrylic acid, methacrylic acid; methacrylates such as methyl methacrylate, ethyl methacrylate, glycidyl methacrylate, butyl methacrylate, allyl methacrylate, lauryl methacrylate, hydroxyethyl methacrylate, chloromethyl methacrylate, 1,3-butylene dimethacrylate; acrylamides such as acrylamide, N-methyl acrylamide, methacrylamide; vinyls such as styrene, acrylonitrile, vinyl pyrrolidone; etc.

The ethylenically unsaturated materials preferred in the preparation of the graft polymers are selected from the group consisting of acrylates, preferably the alkyl acrylates, and methacrylates. The alkyl acrylates are preferably selected from n-butyl acrylate, methyl acrylate, and ethyl acrylate. The methacrylate is preferably methylmethacrylate. The term "alkyl" as used herein refers to alkyl groups of 1 to 10 (preferably 1 to 8) carbon atoms. Most preferred alkyl groups have 1 to 4 carbon atoms.

The ethylenically unsaturated materials may be grafted individually to the cellulosic fibers, or they may be grafted in mixtures, for example, by using one or more of the ethylenically unsaturated materials such as a mixture of methyl methacrylate and n-butyl acrylate.

Essentially fully bleached cellulose, that is wood pulp, is known and has been identified by the geographic area from which the wood comes and the process by which it is bleached. Examples of such wood pulps include Grand Prairie, Prince George, Buckeye Cellulose, and Harmac wood pulps.

Graft copolymers useful in the invention may be formed by free radical initiated processes and by ionic initiated processes. In the former processes, free radical sites may be formed on the cellulose fibers by ionizing radiation, oxidation, formation of unstable metal complexes which lead to one electron transfer from the cellulose to the metal, and redox systems. Typical forms of ionizing radiation include gamma radiation from $^{60}$Co, X-rays, and high energy electrons or electron beams. Oxidative techniques include treatment of cellulose with oxidizing chemicals such as benzoyl peroxide, N,N-azobisisobutyronitrile, potassium thiosulfate, hydriodic acid, activated manganese dioxide, and ferric sulfate and sulfurous acid. Ceric ion initiation is a major example of metal complexation and one electron transfer from cellulose to the metal. Redox systems may be exemplified by treatment of cellulose with ferrous ammonium sulfate followed by immersion in hydrogen peroxide in the presence of vinyl monomers.

The copolymerization reaction is generally conducted either in solution phase or emulsion by the addition of the ethylenically unsaturated material to the cellulose before, during, or after the formation of free radicals on the cellulose. Typical solvents include water, salt solutions such as aqueous zinc chloride, methanol, acetone, dimethylsulfoxide and N,N-dimethylformamide. Copolymerization reactions on cellulose can also be conducted in the solid phase by application of the ethylenically unsaturated material to cellulose from solution, evaporation of solvent, and initiation of graft copolymerization by ionizing radiation. Additional copolymerization techniques are discussed in a review entitled "Grafting Studies on Cotton Cellulose," by Jett C. Arthur, Jr., found in J. Macromol. Sci-Chem., A10(4), pp. 653–670 (1976). Graft polymerization of methyl methacrylate to cellulose in the presence of ceric ion has been described in Journal of Polymer Science 7, 1393 (1969).

Graft polymerization with ceric ion may be carried out according to the following procedure.

Bleached cellulose is dispersed in water by agitation and one or more ethylenically unsaturated monomers are stirred into the dispersion. It is preferred to use a slightly water-soluble monomer such as a methyl or ethyl acrylate or methacrylate to improve the graft efficiency of a less water-soluble monomer such as a propyl or n-butyl acrylate or methacrylate. Usually the more water-soluble monomer is employed in a lesser amount, e.g., in the range of 5 to 20%. A useful monomer mixture is 90% n-butyl acrylate and 10% methyl methacrylate.

The ratio of cellulose to ethylenically unsaturated monomer(s) is preferably in the range of about 70:30 to 30:70 parts by weight cellulose. Cellulose levels in this range produce fibers which provide optimum adhesion to the insect control agent. More preferably the ratio of cellulose to monomer is between about 40:60 and 60:40 (most preferably about 50:50) parts by weight.

Graft copolymerization is initiated by, for example, ceric ammonium nitrate. During graft copolymerization the pH of the polymerization mixture should be carefully controlled. Preferably it is maintained in a pH range of 1.0 to 2.0. Most preferably it is about 1.5. The appropriate pH may be obtained with a suitable acid such as dilute nitric acid, e.g., about 1.0M.

The amount of ceric ammonium nitrate used is preferably 1 to 5 weight percent of the total weight of the fiber-forming materials, and most preferably 2.0 to 3.0 weight percent. As the copolymerization proceeds, the color of the mixture gradually changes from yellow to colorless indicating that the ceric (+4) ion is being reduced to cerous (+3) ion. Once all of the ceric ion has been reduced, the reaction mixture is neutralized to about pH 7 with a weak base such as sodium carbonate and the graft copolymer is isolated as white fibers by, for example, filtration. Any undesired by-products may be removed by, for example, extraction with a suitable solvent such as tetrahydrofuran. Using this process, graft efficiencies and conversion rates of 80% or more may generally be obtained. The product may be washed with water to remove traces of reacted or unreacted contaminants.

The polymerization is preferably carried out in a nitrogen atmosphere in water. The amount of water is generally 90 weight percent or more of the polymerization mixture. Polymerization occurs readily at ambient temperatures, e.g., 15° C. to 30° C. without external temperature control. It is slightly exothermic.

A wide variety of insect control agents is useful in the present invention. Useful agents self-adhere to the fiber surface without the application of external adhesives and, preferably, have a broad spectrum and extended duration of activity. Additionally, they preferably are acceptable in the environment.

Preferred insect control agents for use in the present invention are oleaginous liquids. Most preferably they are microencapsulated in a porous shell permeable to the liquid. In operation, the insect control agents provide an effective amount of the agent in the area surrounding the fiber.

In the preferred case, the oleaginous insect control agents permeate the microcapsule shell wall and provide an effective amount of the agent on the exterior of the microcapsule. The oily character of the agent causes the microcapsule to adhere to the rough-surfaced fiber. Adhesion is enhanced by the oleophilicity of the preferred fiber. The oleophilicity of the preferred fibers facilitates the delivery of the oleaginous insect control agent to the vapor phase from a microcapsule due to their surprising wicking effect on the insect control agent. The contents of the microcapsules are slowly released to the outer surface of the shell wall of the microcapsules. The fibers absorb or wick the released contents and provide maximum exposure of the contents so that they may vaporize and be released to the atmosphere in the most efficient manner. A relatively high level of active vapor is maintained for very extended periods in the vicinity of the devices and compositions of the invention which act to control insect activity in the vicinity of the devices and compositions of the invention.

A preferred class of microencapsulated insect control agents are disclosed in U.S. Pat. No. 4,056,610, the disclosure of which is incorporated herein by reference. This patent discloses compositions comprising a porous microcapsule shell encapsulating a pyrethroid capable of permeating the shell wall. Pyrethroids include the synthetic pyrethroids, such as resmethrin, as well as all of the naturally-occurring pyrethroids. Pyrethroids are oleaginous materials.

In addition to the pyrethroids, the compositions disclosed in U.S. Pat. No. 4,056,610 may include a water-immiscible organic solvent, an antioxidant, a biological synergist, and a first stabilizer capable of absorbing ultraviolet light and having a log molar extinction coefficient of from about 2 to 5 with respect to radiation having wavelengths in the range of from about 270 to 350 nanometers. Additionally, the shell walls of the microcapsule comprise a polyurea which may include as an integral part thereof a second stabilizer capable of absorbing ultraviolet light and having a log molar extinction coefficient of from about 2 to 5 with respect to radiation having wavelengths in the range of from about 270 to 350 nanometers.

The pyrethroids, particularly when encapsulated, possess particularly desirable characteristics. They are among the safest effective insecticides for use around mammals and they have a broad spectrum of activity. When encapsulated as described in U.S. Pat. No. 4,056,610 they are stable and maintain their structural integrity and insect control activity for extended periods of time. Additionally, the permeability of the microcapsules can be varied to provide varying rates of delivery of pyrethroid while maintaining the characteristic of long insect control activity. This property is particularly advantageous since outside the protected environment of the microcapsule pyrethroids have a relatively short half-life. Additionally, the encapsulated pyrethroids adhere firmly to the preferred fibers to provide useful, long-life, strong durable and environmentally resistant devices.

The quantity of insect control agent utilized in the invention can vary. Preferably, it comprises at least about 5, most preferably from about 5 to 50, percent by weight of the total composition. At the higher loadings, insect control activity is obtained more readily. At the lower loadings, the persistence of activity is not significantly changed, although the devices and compositions function more as repellents.

It is generally considered necessary to contact insects with pyrethroids in order to obtain control of their activity. However, the compositions and devices of the present invention provide the pyrethroids primarily as vapors in the area surrounding the devices. Only an insignificant amount of the pyrethroids are provided as either contact liquids or as removable microcapsules.

The insect control agent may be incorporated onto to the rough-surfaced fiber by a variety of techniques. For example, it can be combined with a slurry of the rough-surfaced fiber after which the slurry may be formed and pressed into a sheet like material and dried. A specific example of this technique involves the following operations.

The rough-surfaced fiber, for example the graft copolymer of cellulose and ethylenically unsaturated material, is first refined by beating it in paper-making equipment. This may be accomplished by preparing a dispersion comprising from about 2 to 8 percent by weight of the fiber and correspondingly from about 98 to 92 percent by weight water and beating the resulting dispersion for 10 to 60 minutes. The dispersion may then be combined with the insect control agent, such as an emulsion of the microencapsulated insect control material and hand sheets or paper stock may be prepared by standard paper-making methods. For example, the mixture may be formed and pressed into flat hand sheets (20 cm × 20 cm) by pressing it between sheets of absorbent paper stock at a platen pressure of from about 20 to 80 lb (9 to 36 kg) followed by drying on a paper-making mandrel for from about 3 to 5 minutes at 100° F. to 120° F. (38° C. to 50° C.).

Smooth-surfaced fibers do not act as good sites for adhesion of microencapsulated insect control agents. Scanning electron photomicrographs of blends of smooth-surfaced and rough-surfaced fibers show a preferential adhesion of the microcapsules to rough-surfaced fibers with less than 1% of the microcapsules adhering to smooth-surfaced synthetic fibers. Surprisingly, the smooth-surfaced branches of the graft copolymers do not have an adverse effect on the adhesion of microcapsules. It is thought that this unexpected result is due, at least in part, to forces of capillary pressure which are developed when the capsule contents permeate the shell wall and fill the roughened areas on the fiber surface adjacent to the capsule. It is further thought that the smooth-surfaced branches of the graft copolymers assist in wicking the capsule contents along the rough surfaces of the rough-surfaced fibers.

The devices and compositions of the invention continue to function effectively for extended periods. Examination of a representative device according to the invention showed that after two years of testing, over 70% of the original active contents of the capsule remained in the device. Furthermore, it was observed that the device maintained its structural strength and ability to function for control of insect activity.

Additionally, it was found that even though the preferred embodiments of the invention comprise a significant amount of cellulosic material, they were highly resistant to attack by various indigenous microbes such as bacteria, fungi or molds. No evidence of bacterial, fungal or mold attachment was apparent after outdoor field testing as determined by visual inspection.

In order to provide optimum control of insect activity with the devices of the invention, it is preferred to maximize the surface area of the device exposed to the environment. This may be accomplished by providing the compositions of the invention as webs, tapes, sheets, pads and various other relatively flat configurations. The shape of such devices will generally be such as to allow use in a particular location, for example, a circular sheet for the top of a silo or a ribbon-like tape for placement along the base of a building or door or a rectangular sheet with both sides exposed to maximize the vapor released in a given adjacent area. The devices of the invention may be bonded or glued to a backing to provide for attachment to a surface by the use of an adhesive or other attaching means. Alternatively, sheets of the compositions could be suspended through an eyelet or hole in the sheet by any hanging means. Suspension of a sheet of the composition of the invention maximizes exposure of the fibers to promote vaporization of the pyrethroid insecticide. The compositions and devices of the invention could also be placed in a holder which would contain an eyelet or hole for the purpose of permitting the resulting structure to be suspended.

The present invention is particularly useful in controlling insect activity in structures, such as telephone pedestals, pump houses, and the like, which are expected to be left unattended for extended periods, yet where someone must intermittently install or repair equipment. Such structures invariably have various small openings, cracks, and crevices which allow insects to enter and, if they so choose, establish a residence. It has been found that devices of the present invention are particularly effective in keeping such structures free from insects even when they are located out-of-doors. Thus, such structures can be opened without fear of attack by insects from within.

It has also been found that by hanging or attaching a composition or a device of the invention near an insect nest or home, the insects may be driven away without the use of insecticides which are harmful to humans and other animals, and with minimal cost and minimal danger to the user.

Still further, the compositions and devices of the invention prevent the ingress of crawling insects into buildings when a strip or tape of the compositions of the invention are placed around the base and/or other openings such as windows, doors and vents of the building. This is a good method of either preventing insects from entering roof ventilators or driving out insects using such vents as access to a nest inside a building.

Yet another method of use of the compositions of the invention is to provide them in solution, or preferably, suspension. In this form the compositions may be applied to a surface so that, after evaporation of the liquid carrier, a quantity of the compositions remains in place. It is particularly advantageous to provide the compositions of the invention in this manner when no simple means of attachment of a device of the invention is available, e.g., on soil, on asphalt or concrete surfaces, and the like.

It is preferred that the devices and compositions of the invention be packaged to minimize or eliminate exposure to light. Suitable packaging materials include Scotchpak ®, a product of 3M, St. Paul, Minn. It is generally preferred to place the packages in a carton, box or paper envelope to minimize exposure to light and air so as to minimize degradation and vaporization.

The following examples are provided to illustrate in more detail the practice of the invention. They are not intended to either limit the invention or illustrate all of its variations.

EXAMPLE 1

Synthesis of Cellulose Graft Copolymer

Cellulose (200 g, Harmac fully bleached Douglas Fir pulp available from MacMillan Bloedel, Stamford, CT) was dispersed in water (9.5 l) by mechanical agitation under nitrogen purging for two hours. A mixture of butyl acrylate (200 g) and methyl methacrylate (20 g) was vigorously stirred into the pulp for one-half hour. Graft copolymerization was initiated by addition of ceric ammonium nitrate (11 g, 0.02M) in 1M nitric acid (500 ml). The graft copolymerization was allowed to proceed for four hours, during which the color of the aqueous portion went from yellow ($Ce^4$) to colorless ($Ce^3$) indicating the oxidation of cellulose and initiation of polymerization. The reaction was neutralized with sodium carbonate (26.5 g, 0.25 M), filtered by suction, and washed with water (5 l). The sample was dried overnight at 90° C. to give a white fiber product (405 g, 93% conversion). The cellulose graft copolymer was extracted by refluxing with tetrahydrofuran (9 l) for three hours to remove homopolymer, filtered and dried to yield cellulose/butyl acrylate/methyl methacrylate fibers (200 g/177 g, 53 wt. % cellulose/47 wt. % butyl acrylate/methyl methacrylate, 86% graft efficiency).

EXAMPLE 2

Preparation of Refined Pulp From Grafted Cellulose Copolymer

A cellulose/butyl acrylate/methyl methacrylate graft copolymer (49 wt. % cellulose, 51 wt. % butyl acrylate/methyl methacrylate, 380 g) was dispersed in water (21 l) and refined at various levels for up to 45 minutes using commercially available paper-making equipment (e.g. such as that made by Valley Iron Works). Handsheets (20 cm×20 cm) were prepared from the aqueous slurry (600 ml), pressed at 50 lb (22.7 kg) platen pressure and characterized as shown in Table I. The sheets were conditioned according to ASTM D 645-67.

TABLE I

| | Refining | | | |
|---|---|---|---|---|
| | A | B | C | D |
| Idle Beat (min) | 15 | 15 | 15 | 15 |
| Med. Soft (min) | — | 10 | 20 | 30 |
| Williams Freeness (sec) | 4.5 | 5 | 6 | 7 |
| Properties | | | | |
| Basis weight ASTM D 646-67 (g/m$^2$) | 301 | 241 | 210 | 249 |
| Thickness ASTM D 645-61 (mils) | 40 | 29 | 21 | 23 |
| Dry Tensile ASTM D 828-60 (lbs/in) | 3.1 | 8.9 | 11.3 | 12.4 |
| Internal Tear Resistance[a] ASTM D 689-79 (g/ply) | 132 | 140 | 96 | 64 |
| % Elongation | 5.8 | 5.9 | 5.7 | 6.1 |

TABLE I-continued

| | Refining | | | |
|---|---|---|---|---|
| | A | B | C | D |
| ASTM D 987-48T | | | | |

(a)Elmendorf Tear Tester Model 60-200

EXAMPLE 3

An aqueous slurry prepared as described in Example 2B (600 ml) was combined with an aqueous microencapsulated pyrethrum emulsion (Sectrol® available from 3M Company) (104 g, 11.5 weight percent capsule fill), formed into a handsheet, pressed at 30 lb (13.6 kg) platen pressure for 30 seconds, and dried 3 minutes on a paper-making mandrel. The handsheet (20 cm×20 cm) weighed approximately 16 g and contained 27 weight percent liquid fill from the microcapsules as determined by extraction with dichloromethane.

The handsheets were trimmed to approximately 17.5 cm by 20 cm and packaged in Scotchpak® available from 3M Company. Seven devices were prepared.

The devices were tested in South Florida after removal of the Scotchpak® and installed on the inside of doors of seven individual telephone pedestals which had been cleaned of spider webs, dead insects and frogs. The devices were mounted so that they could hang free on the pedestal doors.

The devices were periodically removed from the pedestals and subjected to laboratory analysis. All pedestals were inspected each time a device was removed for analysis. On each occasion no insects or signs of insect infestation were found and distinct pyrethroid odor was noted. The devices changed color gradually over 24 months from light yellow to golden brown, but remained fully functional.

The devices were analyzed for percent fill both before being sent to Florida initially and when subjected to periodic laboratory analysis. The percentages of liquid fill remaining after each periodic laboratory analysis are given in Table II.

TABLE II

| Time (Mos) | Liquid Fill as Percent of Original |
|---|---|
| | Percent Remaining |
| 0 | 100 |
| 9 | 87 |
| 12 | 82 |
| 18 | 79 |
| 24 | 73 |

This example demonstrates that the devices of the invention provide insect control over an extended period of time.

EXAMPLE 4

Various levels of loading of microencapsulated insecticide on devices of the invention were provided.

Using the method of Example 1, copolymers of 53 weight percent bleached cellulose, 47 weight percert butyl acrylate (9 parts) and methyl methacrylate (1 part) were prepared. Using the methods of Example 2B a pulp of the copolymer was prepared. Using the method of Example 3, 600 ml of the aqueous slurry of the above copolymer were combined with various aqueous suspensions of microencapsulated pyrethrum, the capsules being commercially available as Sectrol® insecticide from 3M Company.

The processing was carried out by varying the length of time of beating at the idle beat setting of the paper-making machine (a commercially available machine made by Valley Iron Works) and by varying the length of time of beating at the minimum beat setting. After the devices had been prepared and dried, they were extracted exhaustively using a Soxhlet apparatus with dichloromethane. The devices were then reweighed dry to determine weight loss. The material that had been extracted was recovered by evaporation of the solvent and weight corrected for polymer present. The percent of capsule fill extracted showed the loading of microencapsulated insecticide which had been achieved, and is shown in Table III.

Table III shows that incorporation of microcapsules into the devices is improved by adjusting the processing (i.e., mixing) duration, and that up to 40 weight percent loading was achieved. This data also shows that the percentage of loading and capsule retention increases with processing.

TABLE III

| Sample No | Sectrol® (g) | Processed according to Ex. | % Active Ingredients Incorp. | Wt. % Active Ingredients in Sample |
|---|---|---|---|---|
| 1 | 0 | 2A | 0 | 0 |
| 2 | 2 | 2A | 30 | 4.3 |
| 3 | 52 | 2A | 35 | 8.0 |
| 4 | 104 | 2A | 35 | 15 |
| 5 | 0 | 2B | 0 | 0 |
| 6 | 26 | 2B | 55 | 10 |
| 7 | 52 | 2B | 51 | 15 |
| 8 | 104 | 2B | 70 | 38 |
| 9 | 0 | 2C | 0 | 0 |
| 10 | 26 | 2C | 100 | 18 |
| 11 | 52 | 2C | 92 | 27 |
| 12 | 104 | 2C | 81 | 34 |
| 13 | 0 | 2D | 0 | 0 |
| 14 | 26 | 2D | 91 | 19 |
| 15 | 52 | 2D | 100 | 26 |
| 16 | 104 | 2D | 97 | 41 |

EXAMPLE 5

To test the durability and microcapsule retention of various fiber matrices loaded with microcapsules, various microcapsule-loaded matrices were cut into 10 cm×12.5 cm pads. The pads were weighed then suspended in a beaker containing one liter of water. The beaker was equipped with a magnetic stirring bar operating at medium speed which provided gentle water flow through the pad. After 15 minutes the pads were removed, dried and weighed. The water was filtered through a nylon screen (0.16 cm² mesh) to collect disintegrated pad fibers. The water was then filtered through filter paper to collect the microcapsules. The dried microcapsules were weighed.

The matrices used to provide pads of fiber mixtures were prepared as follows. About 2 liters of an aqueous slurry of 50/50 (by weight) polymer/cellulose was placed in a paper handsheet former. The slurries were about 2% by weight of fiber. To this slurry was added 100 ml of a mixture of several aqueous slurries of Sectrol®. When the water was drained from the handsheet former, a fiber handsheet matrix was formed on the screen scrim. These matrices were then used to make the pads used in the present example. The matrices were examined with a scanning electron microscope. The results of these tests are shown in Table IV.

The results show that only with cellulosic fibers did the capsules adhere to the fibers.

TABLE IV

Durability Tests

| Matrix | % Capsules Removed | Microscopic Exam. | % Void Volume |
|---|---|---|---|
| Polyester/cellulose[a] | 7 | Capsule aggregates attached to cellulose; smooth, long fibers of polyester bare. | 86 |
| Polyethylene/cellulose[a] | 3 | Most capsule aggregates attached to cellulose; short, fibers of polyethylene bare. | 61 |
| Nylon/cellulose[a] | 4 | Long, smooth, bare fibers of nylon; Cellulose fibers with many attached capsules | 92 |
| Polyvinylalcohol/cellulose[a] | 4 | Bare, smooth fibers of polyvinyl alcohol; Capsule aggregates attached to cellulose | 76 |
| Rayon/cellulose | 1 | A few single capsules attached to rayon; capsule agglomerates attached to cellulose | 84 |
| Scotchbrite ®[b] | 100 | No fibers with capsule aggregates attached | 95 |
| Grafted cellulose | 0 | Capsules attached to graft polymer. | 76 |

[a]Pads disintegrated when removed due to lack of wet strength.
[b]Prepared according to Example, U.S. Pat. No. 4,103,450.

EXAMPLE 6

An insecticidal device was made using the method described in U.S. Pat. No. 4,103,450, Example 1. A non-woven web of dimensions 10 cm by 12.5 cm by 0.94 cm, as described in that example, was impregnated with 0.11 g of Sectrol ® brand insecticide from an aerosol and then dried. This device was identified as device A.

Similarly, another non-woven web was dip-coated with a maximum loading of Sectrol ® brand insecticide and drip dried. This device was identified as device B.

A third device of grafted cellulose was cut to the dimensions 10 cm by 12.5 cm from a handsheet prepared as described herein in Example 3. This device was identified as device C.

Each of the devices was treated in the same manner. Each device was weighed and then placed in a beaker containing one liter of water at about 20° C. The water was stirred with a magnetic stirring bar for 15 minutes after which the pad was hung over the beaker to drip dry and then weighed. The wash water was filtered to obtain the capsules which were dried at room temperature (about 20° C.) overnight, then weighed. The results are shown in Table V.

TABLE V

| Device | Weight Loss of Capsules After Water Wash |
|---|---|
| A | 100 |
| B | 85 |
| C | 0 |

EXAMPLE 7

An aqueous slurry of cellulose/butyl acrylate/ethyl methacrylate graft copolymer (53 weight percent celulose/47 weight percent butyl acrylate/ethyl methacrylate) was refined as described in Example 2B. The aqueous slurry (600 ml) was combined with an aqueous microencapsulated resmethrin emulsion. Resmethrin is a synthetic pyrethroid formulation of not less than 40 weight percent 2,2-dimethyl-3-(2-methyl-1-propenyl)-cyclopropane carboxylic acid [5-(phenylmethyl)-3-furanyl]methyl ester and is available as SBP-1382, S. B. Penick and Company, New York, N.Y.). The microencapsulated resmethrin was prepared according to the teachings of U.S. Pat. No. 4,056,610. The resmethrin was incorporated at various levels to give handsheets of 5 to 35 weight percent active insecticide as described and characterized in Example 3. The resulting devices were useful as insect control devices.

What is claimed is:

1. A device comprising a plurality of rough-surfaced cellulosic fibers which comprise a graft of copolymer cellulose and an ethylenically unsaturated material copolymerizable with cellulose, wherein there is self-adhered to the surface of said fibers an insect control agent comprising a liquid insecticide composition microencapsulated in a capsule whose shell is permeable to said liquid insecticide, said device being formed into an insect control device.

* * * * *

UNITED STATES PATENT AND TRADEMARK OFFICE
CERTIFICATE OF CORRECTION

PATENT NO. : 4,765,982

DATED : August 23, 1988

INVENTOR(S) : RONNING, Patricia M. et al.

It is certified that error appears in the above-identified patent and that said Letters Patent is hereby corrected as shown below:

Column 7, line 38, "inventior" should be -- invention --.

Column 12, line 22, "celulose/47" should be -- cellulose/47 --.

Signed and Sealed this

Twenty-seventh Day of December, 1988

Attest:

DONALD J. QUIGG

*Attesting Officer*  *Commissioner of Patents and Trademarks*